United States Patent
Martinelli et al.

(10) Patent No.: US 11,673,860 B2
(45) Date of Patent: Jun. 13, 2023

(54) CRYSTALLINE SIPONIMOD FUMARIC ACID AND POLYMORPHS THEREOF

(71) Applicant: TEVA PHARMACEUTICALS INTERNATIONAL GMBH, Jona (CH)

(72) Inventors: Marisa Martinelli, Villa Guardia (IT); Pavel Kolesa, Haj ve Slezsku (CZ); Maurizio Paiocchi, Milan (IT); Matteo Toso, Rescaldina (IT); Roberta Volonté, Rovellasca (IT); Piero Paravidino, Sedriano (IT)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 16/963,424

(22) PCT Filed: Jan. 22, 2019

(86) PCT No.: PCT/US2019/014476
§ 371 (c)(1),
(2) Date: Jul. 20, 2020

(87) PCT Pub. No.: WO2019/144094
PCT Pub. Date: Jul. 25, 2019

(65) Prior Publication Data
US 2021/0087140 A1 Mar. 25, 2021

Related U.S. Application Data

(60) Provisional application No. 62/620,039, filed on Jan. 22, 2018.

(51) Int. Cl.
*C07D 205/04* (2006.01)

(52) U.S. Cl.
CPC ........ *C07D 205/04* (2013.01); *C07B 2200/13* (2013.01)

(58) Field of Classification Search
CPC .......................... C07D 205/04; C07B 2200/13
See application file for complete search history.

(56) References Cited

U.S. PATENT DOCUMENTS

| | | | |
|---|---|---|---|
| 7,939,519 B2 | 5/2011 | Pan et al. | |
| 8,173,634 B2 | 5/2012 | Liu et al. | |
| 8,486,930 B2 | 7/2013 | De La Cruz et al. | |
| 9,604,914 B2 | 3/2017 | Gallou et al. | |
| 11,434,200 B2 | 9/2022 | Huang et al. | |
| 2012/0115840 A1* | 5/2012 | Ciszewski | A61P 37/00 548/953 |
| 2018/0118678 A1 | 5/2018 | Ciszewski et al. | |
| 2021/0323915 A1 | 10/2021 | Ciszewski et al. | |

FOREIGN PATENT DOCUMENTS

| | | |
|---|---|---|
| EP | 2379497 B1 | 12/2009 |
| IN | 201821040743 | 5/2020 |
| IN | 201841040513 | 5/2020 |
| IN | 201841045627 | 6/2020 |
| IN | 201921016502 | 10/2020 |
| IN | 201941043464 | 4/2021 |
| WO | 2010071794 A1 | 6/2010 |
| WO | 2010080409 A1 | 7/2010 |
| WO | 2010080455 A1 | 7/2010 |
| WO | 2013113915 A1 | 8/2013 |
| WO | 2015155711 A1 | 10/2015 |
| WO | 2019064184 A1 | 4/2019 |
| WO | 2020161632 A1 | 8/2020 |
| WO | 2020174408 A1 | 9/2020 |
| WO | 2020234423 A1 | 11/2020 |

OTHER PUBLICATIONS

International Search Report for International Application No. PCT/US2019/014476, International Filing Date Jan. 22, 2019, dated Mar. 27, 2019, 7 pages.
Written Opinion for International Application No. PCT/US2019/014476, International Filing Date Jan. 22, 2019, dated Mar. 27, 2019, 9 pages.

* cited by examiner

*Primary Examiner* — Kamal A Saeed
(74) *Attorney, Agent, or Firm* — Cantor Colburn LLP

(57) ABSTRACT

Disclosed crystalline Siponimod fumaric acid, solid state forms (polymorphs) thereof, processes for preparation thereof and pharmaceutical compositions thereof.

20 Claims, 5 Drawing Sheets

Figure 1: PXRD of Siponimod fumaric acid Form 3
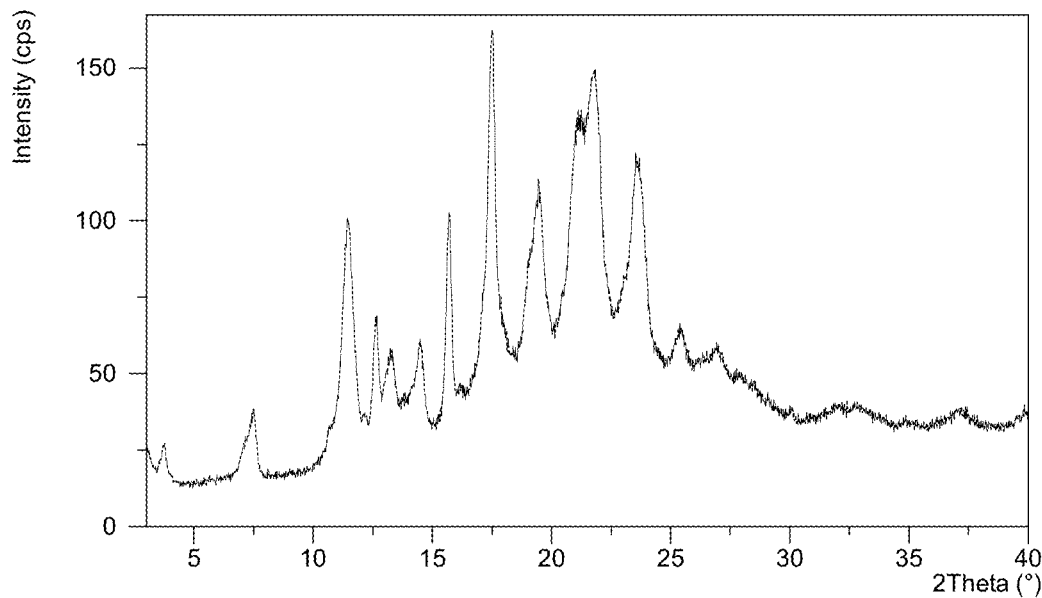
Figure 2: PXRD of Siponimod fumaric acid Form 7
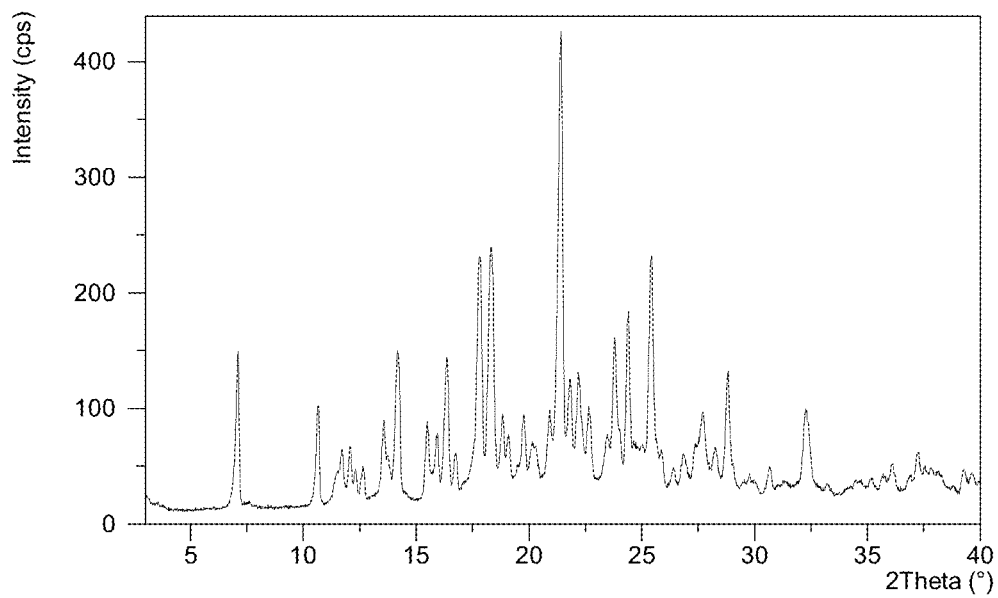

Figure 3: PXRD of the hemioxalate salt of compound A– form I:
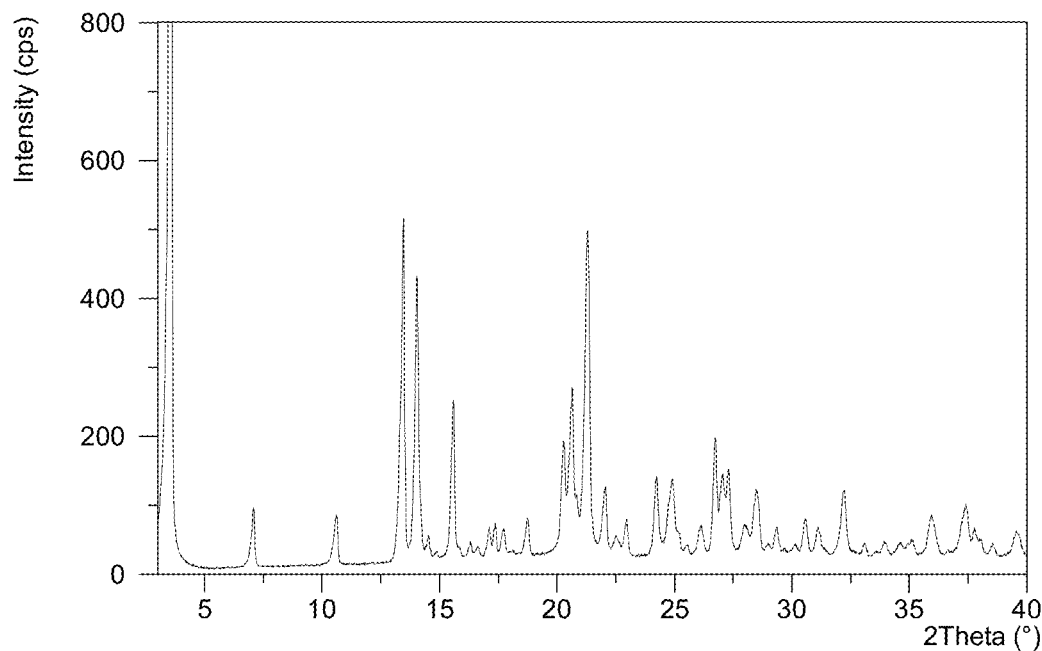
Figure 4: PXRD of the hemioxalate salt of compound A – form II:
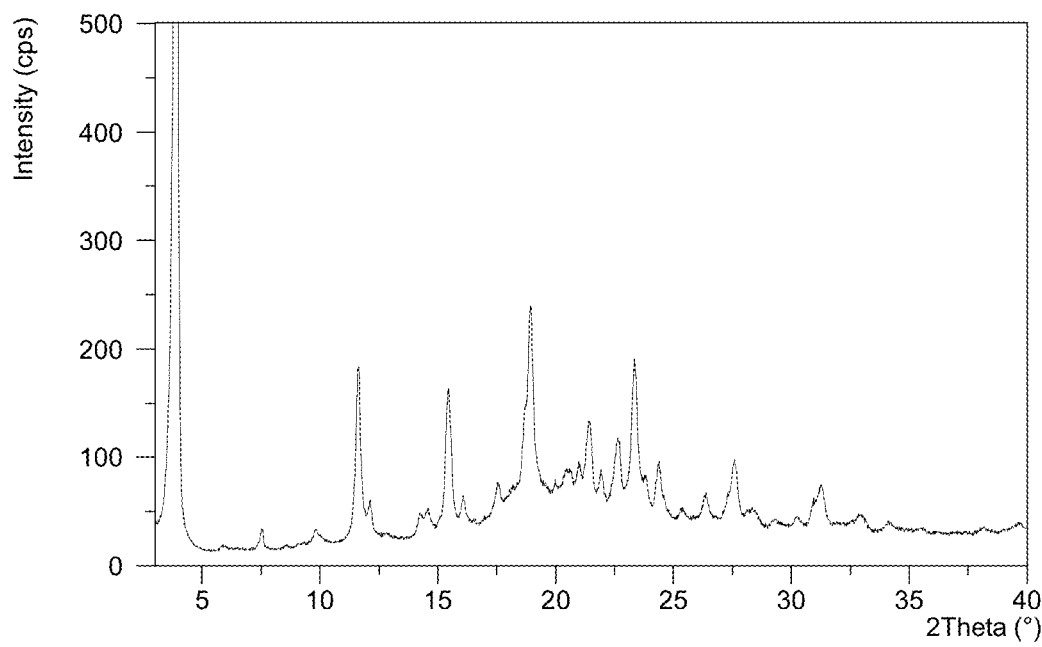

Figure 5: PXRD of the hemioxalate salt of compound A – form III:
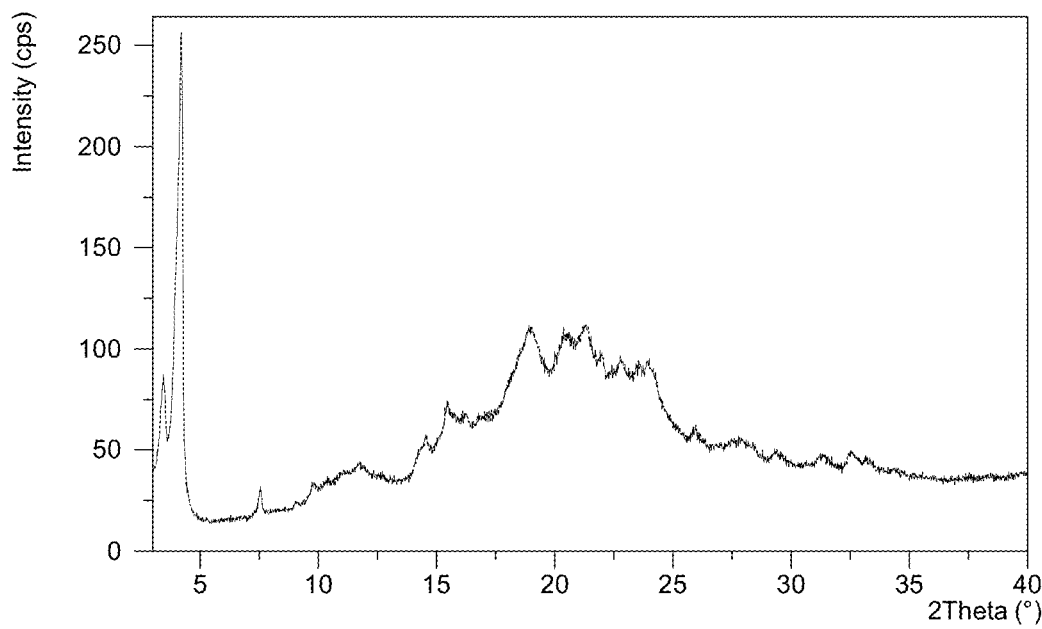
Figure 6: PXRD of the hemioxalate salt of compound A – form IV:
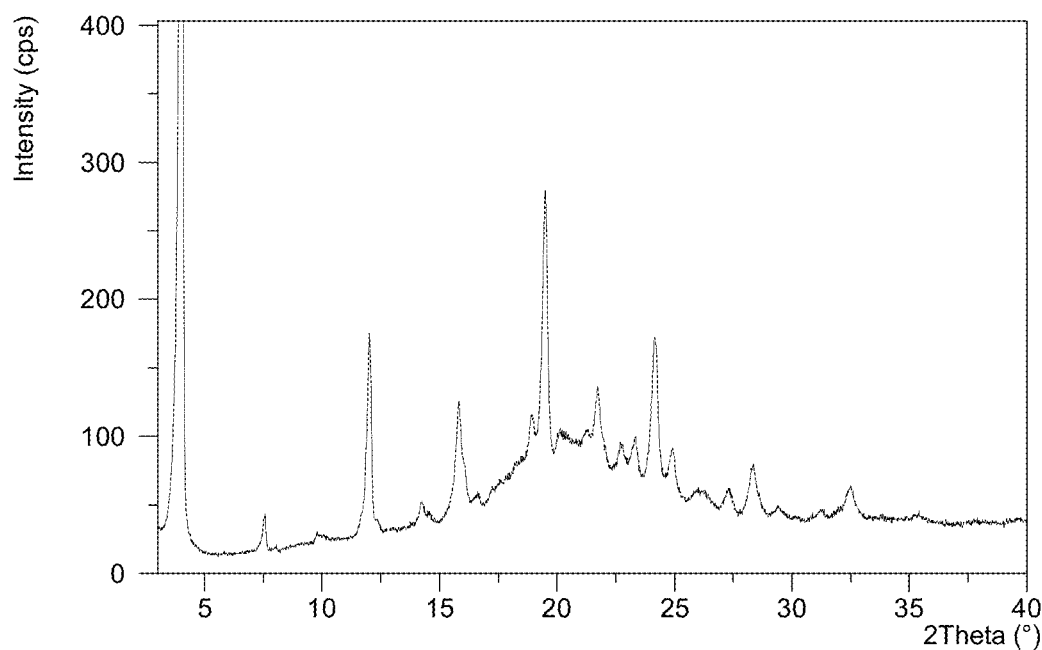

Figure 7: PXRD of the hemioxalate salt of compound A – form V:
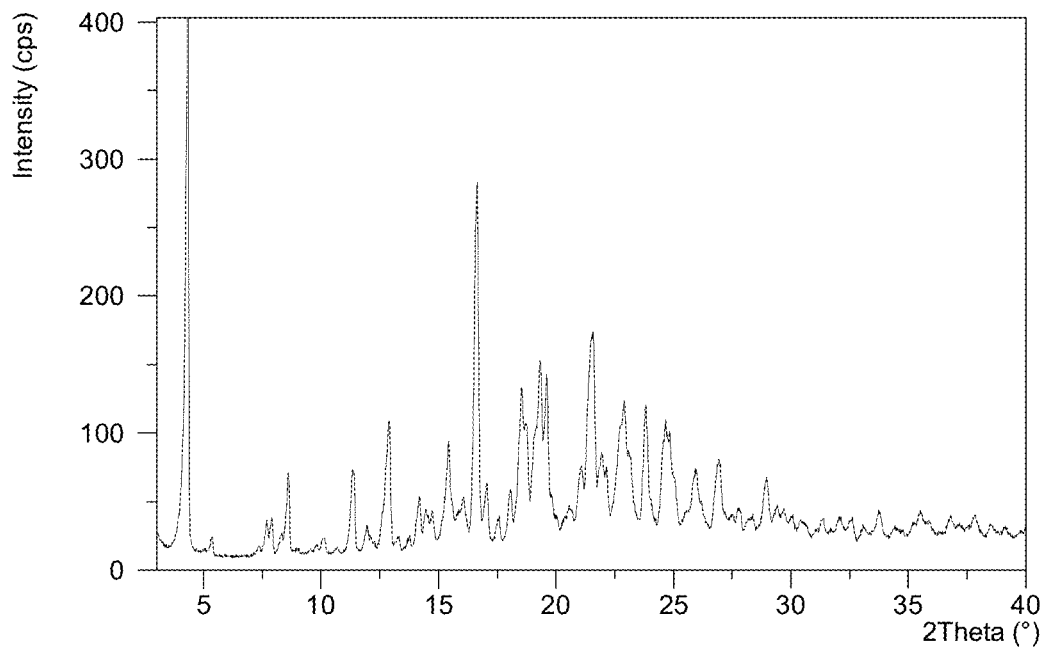
Figure 8: Solid state $^{13}$CNMR spectrum of Siponimod Fumaric acid Form 7:
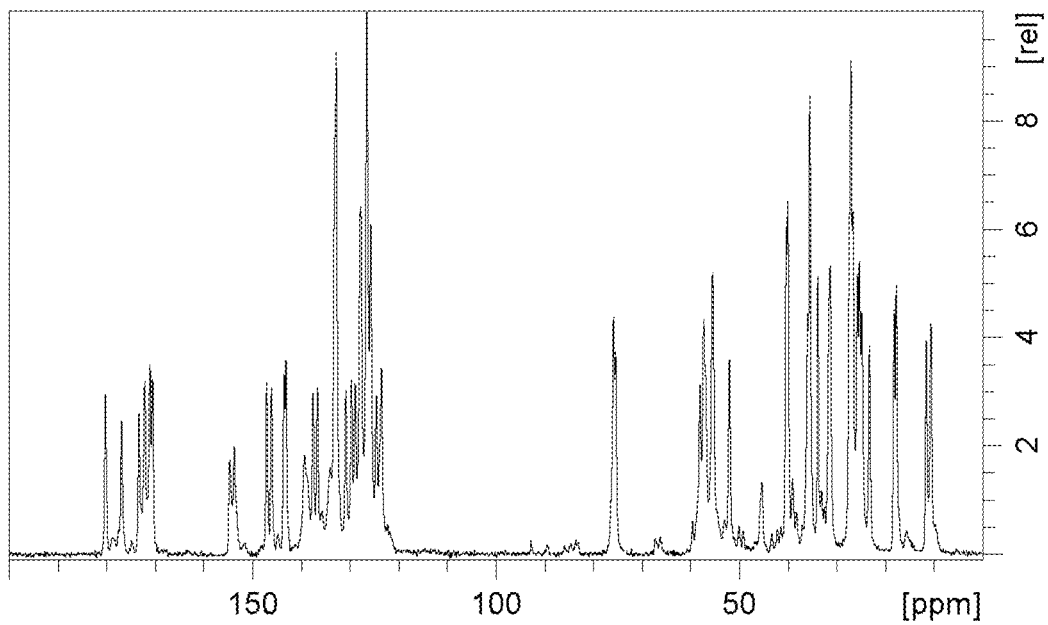

Figure 9: FT-Raman spectrum of Siponimod fumaric acid Form 7:
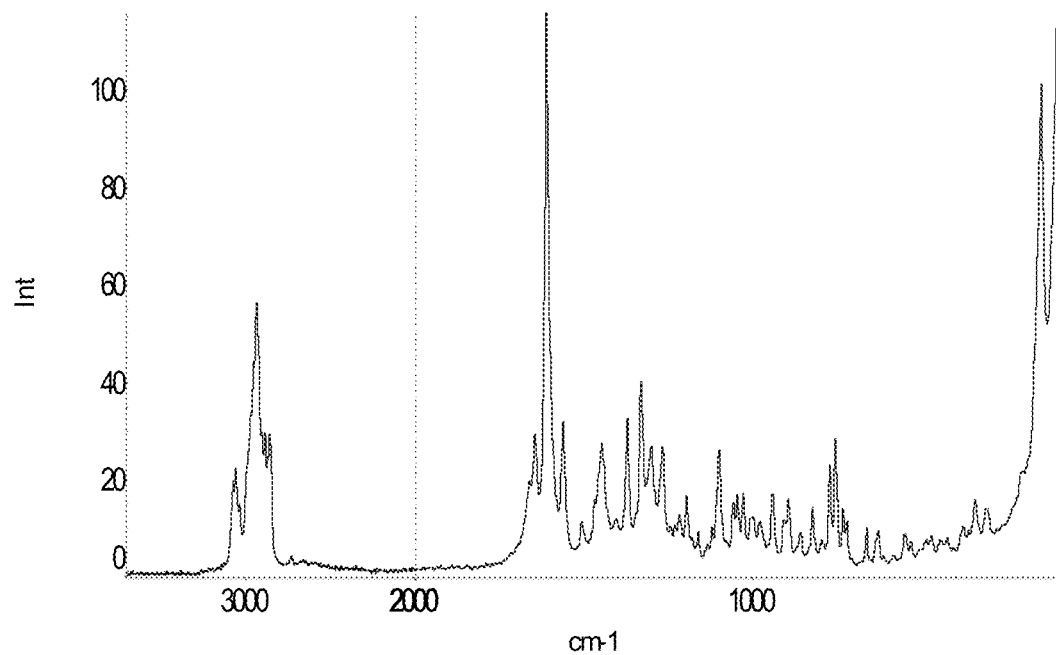

CRYSTALLINE SIPONIMOD FUMARIC ACID AND POLYMORPHS THEREOF

CROSS-REFERENCE TO RELATED APPLICATIONS

This application is a National Stage application of PCT/US2019/014476, filed Jan. 22, 2019, and is related to, and claims the benefit of priority of, U.S. Provisional Patent Application No. 62/620,039, filed Jan. 22, 2018, the contents of each are incorporated herein by reference in their entirety for all purposes.

FIELD OF INVENTION

The present invention relates to crystalline Siponimod fumaric acid, solid state forms (polymorphs) thereof, processes for preparation thereof and pharmaceutical compositions thereof.

BACKGROUND OF THE INVENTION

Siponimod (compound I), 1-(4-(1-(((E)-4-cyclohexyl-3-tri-fluoro-methyl-benzyloxy-imino)-ethyl)-2-ethyl-benzyl)-azetidine-3-carboxylic acid, has the following chemical structure.

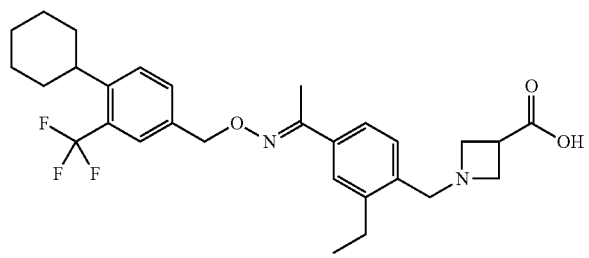

Compund I

Siponimod is a selective sphingosine-1-phosphate receptor modulator for oral use that is currently under development for treating multiple sclerosis (MS).

Siponimod (and pharmaceutical acceptable salts thereof) are known from U.S. Pat. No. 7,939,519. WO2010/080409 discloses the hemifumarate salt of Siponimod and its crystalline forms (polymorphs A to E). U.S. Pat. No. 8,173,634 describes polymorph A of Siponimod base and U.S. Pat. No. 8,486,930 discloses the HCl, Oxalate, Malate and Tartrate salts of Siponimod; and crystalline forms thereof.

U.S. Pat. No. 9,604,914 discloses a process for preparing compound II, which is used as an intermediate in the preparation of Siponimod.

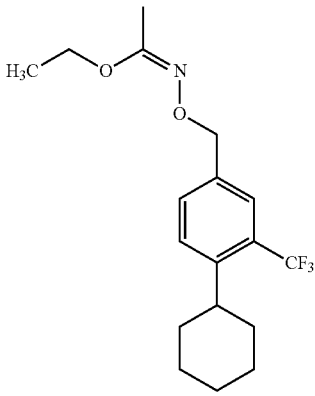

Compound II

Polymorphism, the occurrence of different crystal forms, is a property of some molecules and molecular complexes. A single compound, like Siponimod, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms, co-crystals and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms, co-crystals and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms of Siponimod fumaric acid which offer superior physico-chemical properties (such as thermodynamic stability) without altering the pharmacological properties.

SUMMARY OF THE INVENTION

The present invention relates to crystalline Siponimod fumaric acid, solid state forms (polymorphs) thereof, to processes for preparation thereof, and to pharmaceutical compositions comprising these solid state forms.

The present invention also provides the use of anyone of the solid state forms of Siponimod fumaric acid for preparing other solid state forms of Siponimod fumaric acid, or salts of Siponimod, and solid state forms thereof.

In another embodiment, the present invention encompasses crystalline Siponimod fumaric acid or any one of the described solid state forms of Siponimod fumaric acid and/or combinations thereof for use in the preparation of pharmaceutical compositions and/or formulations, preferably for the treatment of multiple sclerosis.

The present invention further provides pharmaceutical compositions comprising crystalline Siponimod fumaric acid or any one of or a mixture of the solid state forms of Siponimod fumaric acid according to the present invention.

In yet another embodiment, the present invention encompasses pharmaceutical formulations comprising crystalline Siponimod fumaric acid or any one of the described solid state forms of Siponimod fumaric acid and/or combinations thereof and at least one pharmaceutically acceptable excipient.

The present invention encompasses processes to prepare said pharmaceutical formulations of Siponimod fumaric acid comprising combining crystalline Siponimod fumaric acid or any one of the solid state forms and/or combinations thereof and at least one pharmaceutically acceptable excipient.

In another embodiment the present invention encompasses the use of crystalline Siponimod fumaric acid or any one of the described solid state forms of Siponimod fumaric acid and/or combinations thereof for the preparation of pharmaceutical compositions and/or formulations.

Crystalline Siponimod fumaric acid or any of the solid state forms as defined herein and/or combinations thereof as well as the pharmaceutical compositions or formulations of Siponimod fumaric acid can be used as medicaments, particularly for the treatment of multiple sclerosis.

The present invention also provides a method of treating multiple sclerosis; comprising administering a therapeutically effective amount of crystalline Siponimod fumaric acid or any one of the crystalline forms of Siponimod fumaric acid of the present invention and/or combinations thereof, or at least one of the above pharmaceutical compositions or formulations, to a subject suffering from multiple sclerosis, or otherwise in need of the treatment.

The present invention also provides the use of crystalline Siponimod fumaric acid or any one of the solid state forms of Siponimod fumaric acid of the present invention and/or combinations thereof, or at least one of the above pharmaceutical compositions or formulations for the manufacture of a medicament for treating multiple sclerosis; particularly secondary progressive multiple sclerosis.

In another embodiment; the present invention discloses the hemioxalate salt of O-[[4-cyclohexyl-3-(trifluoromethyl)phenyl]methyl]-hydroxylamine (compound A) and polymorphs thereof.

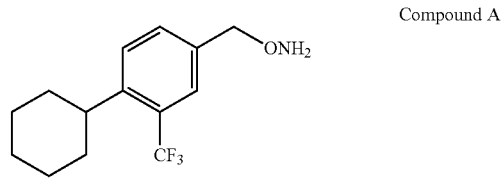
Compound A

The present invention also provides the use of the hemioxalate salt of compound A for preparing Siponimod and salts thereof, including crystalline Siponimod fumaric acid and solid state forms thereof.

BRIEF DESCRIPTION OF THE DRAWINGS

FIG. 1 shows a powder X-ray diffraction pattern ("PXRD" of Siponimod fumaric acid Form 3.

FIG. 2 shows a powder X-ray diffraction pattern of Siponimod fumaric acid Form 7.

FIG. 3 shows a powder X-ray diffraction pattern of form I of the hemioxalate salt of compound A.

FIG. 4 shows a powder X-ray diffraction pattern of form II of the hemioxalate salt of compound A.

FIG. 5 shows a powder X-ray diffraction pattern of form III of the hemioxalate salt of compound A FIG. 6 shows a powder X-ray diffraction pattern of form IV of the hemioxalate salt of compound A FIG. 7 shows a powder X-ray diffraction pattern of form V of the hemioxalate salt of compound A FIG. 8 shows a solid state $^{13}C$ NMR spectrum of Siponimod fumaric acid Form 7.

FIG. 9 shows an FT-Raman spectrum of Siponimod fumaric acid Form 7.

DETAILED DESCRIPTION OF THE INVENTION

The present invention relates to crystalline Siponimod fumaric acid, to solid state forms (polymorphs) thereof, such as crystalline Forms 3 and 7; to processes for preparation thereof and to pharmaceutical compositions comprising crystalline Siponimod fumaric acid or at least one of, or a combination of, the solid state forms. The invention also relates to the conversion of the crystalline forms of the invention to siponimod free base, other solid state forms of Siponimod fumaric acid or to salts of siponimod and solid state forms thereof.

As used herein, crystalline Siponimod fumaric acid refers to a co-crystal of siponimod fumaric acid where the molar ratio of the active pharmaceutical ingredient (siponimod) and the coformer (fumaric acid) is 1:1. The crystalline Siponimod fumaric acid of the present invention may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, and bulk density.

Crystalline Siponimod fumaric acid referred to herein as being characterized by graphical data "as depicted in" a Figure will thus be understood to include any crystal form of Siponimod fumaric acid, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains 20% or less, 10% or less, 5% or less, 2% or less, or 1% or less of any other forms of the subject compound as measured, for example, by PXRD. Thus, solid state forms of Siponimod fumaric acid described herein as substantially free of any other solid state forms would be understood to contain greater than 80% (w/w), greater than 90% (w/w), greater than 95% (w/w), greater than 98% (w/w), or greater than 99% (w/w) of the subject solid state form of Siponimod fumaric acid. Accordingly, in some embodiments of the invention, the described solid state forms of Siponimod fumaric acid may contain from 1% to 20% (w/w), from 5% to 20% (w/w), or from 5% to 10% (w/w) of one or more other solid state forms of Siponimod fumaric acid.

As used herein, unless stated otherwise, PXRD peaks reported herein are preferably measured using CuK$_\alpha$ radiation, $\lambda$=1.54 Å.

As used herein, the term "isolated" in reference to crystalline Siponimod fumaric acid of the present invention corresponds to a crystalline Siponimod fumaric acid that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A processor step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the expression "wet crystalline form" refers to a crystalline form that was not dried using any conventional techniques to remove residual solvent. Examples for such conventional techniques can be, but are not limited to, evaporation, vacuum drying, oven drying, drying under nitrogen flow, etc.

As used herein, the expression "dry crystalline form" refers to a crystalline form that was dried using any conventional techniques to remove residual solvent. Examples of such conventional techniques can be, but are not limited to, evaporation, vacuum drying, oven drying, drying under nitrogen flow, etc.

The term "solvate", as used herein and unless indicated otherwise, refers to a crystal form that incorporates a solvent in the crystal structure. When the solvent is water, the solvate is often referred to as a "hydrate". The solvent in a solvate may be present in either a stoichiometric or in a non-stoichiometric amount.

The amount of solvent employed in a chemical process, e.g., a reaction or crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

The present invention further comprises a crystalline form (polymorph) of Siponimod fumaric acid designated as Form 3. The crystalline Form 3 of Siponimod fumaric acid can be characterized by data selected from one or more of the following: a PXRD pattern having peaks at 12.6, 15.7, 17.5 and 23.4 deg. 2-theta±0.2 deg 2-theta, a PXRD pattern as depicted in FIG. 1; and combinations of these data.

Crystalline Form 3 of Siponimod fumaric acid may be further characterized by the PXRD pattern having peaks at 12.6, 15.7, 17.5 and 23.4 deg-2-theta±0.2 deg. 2-theta, and also having one, two, three, four or five additional peaks selected from 11.5, 13.5, 14.5, 19.5 and 21.9 deg-2-theta±0.2 deg. 2-theta.

The present invention further comprises a crystalline form of Siponimod fumaric acid designated as Form 7. The crystalline Form 7 of Siponimod fumaric acid can be characterized by data selected from one or more of the following: a PXRD pattern having peaks at 16.4, 17.8, 18.3, 22.7, and 25.4 deg. 2-theta±0.2 deg. 2-theta; a PXRD pattern as depicted in FIG. 2; and combinations of these data.

Crystalline Form 7 of Siponimod fumaric acid may alternatively or additionally be characterized by data selected from one or more of the following: a solid state $^{13}$C NMR spectrum with characteristic peaks at 146.1, 136.6, 132.8, 130.8 and 128.9 ppm±0.2 ppm; a solid state $^{13}$C NMR spectrum having the following chemical shift absolute differences from reference peak at 123.5 ppm±1 ppm: 22.6, 13.1, 9.3, 7.3 and 5.4 ppm±0.1 ppm; or by a solid state $^{13}$C NMR spectrum substantially as depicted in FIG. 8; or combinations of these data.

Crystalline Form 7 of Siponimod fumaric acid may be further characterized by the PXRD pattern having peaks at 16.4, 17.8, 18.3, 22.7, and 25.4 deg. 2-theta±0.2 deg. 2-theta and also having one, two, three, four or five additional peaks selected from 13.6, 14.2, 16.8, 21.8 and 24.4 deg-2-theta±0.2 deg. 2-theta; an FT-Raman spectrum having peaks at 1648, 1614, 1564, 1450, 1373, 1332, 1302, 1269, 1198, 1101; an FT-Raman spectrum as depicted in FIG. 9; and combinations of these data.

Crystalline Form 7 of Siponimod fumaric acid may be anhydrous.

Crystalline Siponimod fumaric acid according to the present invention is thermodynamically stable and steady under stressed conditions (e.g., high temperature and relative humidity). Pharmaceutical molecules may display solid to solid phase transformations and transformations between polymorphs; which may detected by exposure of the solid state form to stress conditions of e.g., high temperature and high relative humidity. In particular, crystalline Form 7 of Siponimod fumaric acid according to the present invention has shown to be thermodynamically and chemical stable.

The present invention also provides the use of any one of the solid state forms of Siponimod fumaric acid for preparing other solid state forms of Siponimod fumaric acid, Siponimod salts or Siponimod base, and solid state forms thereof.

In another embodiment the present invention encompasses crystalline Siponimod fumaric or any one of the above described solid state forms of Siponimod fumaric acid and/or combinations thereof for use in the preparation of pharmaceutical compositions, preferably for the treatment of multiple sclerosis.

The present invention further provides pharmaceutical compositions comprising crystalline Siponimod fumaric any one of or a mixture of the solid state forms of Siponimod fumaric acid according to the present invention.

The present invention comprises a process for preparing the above mentioned pharmaceutical compositions.

In yet another embodiment, the present invention encompasses pharmaceutical formulations comprising crystalline Siponimod fumaric or any one of the above described solid state forms of Siponimod fumaric acid and/or combinations thereof and at least one pharmaceutically acceptable excipient.

The present invention encompasses a process to prepare said formulations of Siponimod fumaric acid comprising combining crystalline Siponimod fumaric or any one of the above solid state forms and/or combinations thereof and at least one pharmaceutically acceptable excipient.

In another embodiment the present invention encompasses the use of crystalline Siponimod fumaric or any one of the above described solid state forms of Siponimod fumaric acid and/or combinations thereof for the preparation of pharmaceutical compositions and/or formulations.

Crystalline Siponimod fumaric or any one of the solid state forms thereof as defined herein and/or combinations thereof, as well as the pharmaceutical compositions or formulations of Siponimod fumaric acid can be used as medicaments for the treatment of multiple sclerosis; in particular secondary progressive multiple sclerosis.

The present invention also provides a method of treating multiple sclerosis, comprising administering a therapeutically effective amount of crystalline Siponimod fumaric or any one of the solid state forms of Siponimod fumaric acid of the present invention and/or combinations thereof, or at least one of the above pharmaceutical compositions or formulations, to a subject suffering from multiple sclerosis, or otherwise in need of the treatment.

The present invention also provides the use of crystalline Siponimod fumaric or any one of the solid state forms of Siponimod fumaric acid of the present invention and/or combinations thereof, or at least one of the above pharmaceutical compositions or formulations for the manufacture of a medicament for treating multiple sclerosis; particularly secondary progressive multiple sclerosis.

In another embodiment the present invention provides the hemioxalate salt of compound A. The isolation of compound A as the hemioxalate salt allows the purification of compound A; the isolated solid is sufficiently stable, easy to obtain by filtration and suitable for stocking and handling.

In another embodiment the invention provides form I of the hemioxalate salt of compound A. The crystalline form I of the hemioxalate salt of compound A can be characterized by data selected from one or more of the following: a PXRD pattern having peaks at 3.6, 7.1, 10.6, 13.5 and 21.3 deg-2-theta±0.2 deg. 2-theta; a PXRD pattern as depicted in FIG. 3; and combinations of these data.

Crystalline form I of the hemioxalate salt of compound A may be further characterized by the PXRD pattern having peaks at 3.6, 7.1, 10.6, 13.5 and 21.3 deg-2-theta 0.2 deg. 2-theta and also having one, two, three, four or five additional peaks selected from 14.0, 15.6, 20.3, 20.6 and 22.1 deg-2-theta±0.2 deg. 2-theta.

Yet in a further embodiment the invention provides form II of the hemioxalate salt of compound A. The crystalline form II of the hemioxalate salt of compound A can be characterized by data selected from one or more of the following: a PXRD pattern having peaks at 3.9, 11.6, 18.9 and 23.3 deg-2-theta±0.2 deg. 2-theta; a PXRD pattern as depicted in FIG. 4; and combinations of these data.

Crystalline form II of the hemioxalate salt of compound A may be further characterized by the PXRD pattern having peaks at 3.9, 11.6, 18.9 and 23.3 deg-2-theta±0.2 deg. 2-theta and also having one, two, three, four or five additional peaks selected from 15.5, 21.4, 22.6 and 26.3 deg-2-theta±0.2 deg. 2-theta.

In another embodiment the invention provides form IV of the hemioxalate salt of compound A. The crystalline form IV of the hemioxalate salt of compound A can be characterized by data selected from one or more of the following: a PXRD pattern having peaks at 4.0, 12.0, 15.8 and 19.5 deg-2-theta±0.2 deg. 2-theta; a PXRD pattern as depicted in FIG. 6; and combinations of these data.

Crystalline form IV of the hemioxalate salt of compound A may be further characterized by the PXRD pattern having peaks at 4.0, 12.0, 15.8 and 19.5 deg-2-theta±0.2 deg. 2-theta and also having one, two, three, four or five additional peaks selected from 7.6, 21.7, 24.2 and 24.9 deg-2-theta±0.2 deg. 2-theta.

In a further embodiment the invention provides form V of the hemioxalate salt of compound A. The crystalline form V of the hemioxalate salt of compound A can be characterized by data selected from one or more of the following: a PXRD pattern having peaks at 4.3, 8.6, 11.4, 12.9 and 16.6 deg. 2-theta±0.2 deg. 2-theta; a PXRD pattern as depicted in FIG. 7; and combinations of these data.

Crystalline form V of the hemioxalate salt of compound A may be further characterized by the PXRD pattern having peaks 4.3, 8.6, 11.4, 12.9 and 16.6 deg-2-theta±0.2 deg. 2-theta and also having one, two, three, four or five additional peaks selected from 15.4, 18.5, 19.3, 19.6 and 23.8 deg-2-theta±0.2 deg. 2-theta.

The hemioxalate salt of compound A and polymorphs thereof (as described above) can be used in the preparation of Siponimod and its acceptable salts. The Hemioxalate salt of compound A can be used either as such or after neutralizing the salt for the prosecution of the synthesis according to methods known in the literature (e.g., example 3 of U.S. Pat. No. 7,939,519).

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Powder X-Ray Diffraction Pattern ("PXRD") Method:

Powder X-ray Diffraction was performed on an X-Ray powder diffractometer PanAlytical X'pert Pro; CuKα radiation ($\lambda$=1.54187 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement Parameters:

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

FT-Raman Spectroscopy Method:

Powder samples were filled into 5 mm NMR tube and Raman spectrum was recorded on Nicolet 6700 FT-IR spectrometer with NXR FT-Raman module, equipped with 1064 nm Nd:YVO4 excitation laser, CaF2 beam splitter and Ge detector.

Instrument Parameters:

Spectral range: 3700-100 cm$^{-1}$
Resolution: 4.0 cm$^{-1}$
Number of scans: 128
Sample gain: auto
Optical velocity: 0.4747
Aperture: 59.46
Laser power: 2.0 W $^{13}$C Solid State NMR Method:

$^{13}$C CP/MAS NMR spectra were measured at 125 MHz using Bruker Avance III 500 WB/US NMR spectrometer (Karlsruhe, Germany, 2003) at magic angle spinning (MAS) frequency $\omega_r/2\pi=11$ kHz. In all cases finely powdered samples were placed into 4-mm ZrO$_2$ rotors and the standard "cpmas" pulseprogram was used. During acquisition of the data the high-power dipolar decoupling "TPPM" (two-pulse phase-modulated) was applied. The flip-pulse length was 4.8 µs. Applied nutation frequency of $B_1(^1H)$ field was $\omega_1/2\pi=89.3$ kHz. Nutation frequency of $B_1(^{13}C)$ and $B_1(^1H)$ fields during cross-polarization was $\omega_1/2\pi=62.5$ kHz. The number of scans was 2048. Taking into account frictional heating of the samples during fast rotation all NMR experiments were performed at 293 K (precise temperature calibration was performed).

The NMR spectrometer was completely calibrated and all experimental parameters were carefully optimized prior the investigation of samples. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time).

EXAMPLES

Preparation of Starting Materials:

Siponimod can be prepared according to methods known from the literature (for example U.S. Pat. No. 7,939,519).

Form A (acknowledged in WO2010/080409 as Form A of the hemifumarate salt of compound I) can be prepared according to example 2 of WO2010/080409.

The HCl salt of compound A can be obtained by submitting a solution of N-(4-cyclohexyl-3-trifluoromethylbenzyoxy)-acetimidic acid ethyl ester (prepared e.g. as described in WO2013113915) in an organic solvent (e.g. methanol, isopropanol) to acid hydrolysis using aqueous HCl and completely evaporating the solvent.

Compound A (free base) can be obtained by neutralization of the hydrochloride salt in an organic solvent (using an aqueous solution of NaHCO$_3$) and evaporation of the solution.

Example 1

Siponimod (320 mg, amorphous) was suspended in water (5 ml). After adding solid fumaric acid (36 mg) the suspension was stirred at 50° C. for 1 hour and then at room temperature for 24 hours. The obtained solid (430 mg as wet white powder) was characterized by X-ray powder diffraction—Siponimod fumaric acid Form 3.

Example 2

In a 3 neck cylinder glass reactor (equipped with a condenser) a suspension of Form A, (500 mg) in trifluoroethanol (22 ml) was warmed to reflux until complete dissolution. After cooling to 0° C. within 1 h, the solution was re-heated to reflux and distilled to lower volume (about 5 ml). After cooling to room temperature, water was added dropwise to the clear solution. The stirring was prolonged for 30 minutes; the obtained white solid was filtered (180 mg) and characterized by X-ray powder diffraction—Siponimod fumaric acid Form 7; as shown in FIG. 2.

Example 3

In a flask Form A (100 mg) was dissolved in tetrahydrofuran (THF) (4.5 ml) and water (6.5 ml). The solution was stirred at room temperature for 20 minutes then water (2.5 ml) was added dropwise. The open flask was left in a glove-box under nitrogen atmosphere for 10 days. The obtained precipitate was filtered to afford a white powder (75 mg) that was characterized by X-ray powder diffraction—Siponimod fumaric acid Form 3; as shown in FIG. 1.

Example 4

Form A (0.50 g) was dissolved in a mixture of dichloromethane (2 ml) and methanol (1 ml) by stirring at 40° C.; fumaric acid (0.10 g) was added and the mixture was evaporated to half volume by stirring at 40-50° C. in an open vessel under ambient pressure. The mixture was stirred overnight at 20° C. (closed vessel); the resulting thick mixture was diluted with dichloromethane/methanol 2:1 (about 1 ml) and the precipitate was recovered by filtration to obtain the desired crystalline Form 7 of Siponimod fumaric acid.

Example 5

Form A (0.50 g) was suspended in a mixture of acetone (3 ml) and methanol (1 ml) and stirred at 50° C.; metanol was added until complete dissolution (about 6 ml). Fumaric acid (0.10 g) was added; the mixture was stirred on a hot plate at 70° C. while evaporating the solvent with a gentle nitrogen flow to about half volume, then cooled to 25° C.; the thick suspension was diluted with acetone and the precipitate was recovered by filtration to obtain crystalline Form 7 of Siponimod fumaric acid.

Example 6

Form A (2.0 g) was suspended in a mixture of 2-methyltetrahydrofuran (7 ml) and water (1 ml); the suspension was stirred at 35° C. until a slightly cloudy solution was obtained; the mixture was cooled to 0° C. and then reheated to 35° C. Fumaric acid (550 mg) was added; the resulting mixture was cooled to 0° C. during 2 h and stirred overnight at 0° C. The obtained precipitation was recovered by filtration and dried to obtain Form 7 of Siponimod fumaric acid (1.5 g).

Example 7

Siponimod (5.0 g) was dissolved in a mixture of 2-methyltetrahydrofuran (47 ml) and water (3 ml) at 20° C., followed by the addition of fumaric acid (2.7 g). The solvent was distilled at 30° C. under vacuum until about 35 ml of residual volume left and then seeded with crystalline Form 7 of Siponimod fumaric acid (prepared according to any of the above examples, 100 mg); more solvent was removed by distillation until about 22 ml of residual volume left, then more seeds of crystalline Form 7 were added (100 mg); finally the mixture was cooled to 0° C. during 2 h and stirred at the same temperature overnight. The precipitate was collected by filtration and dried under vacuum at 40° C. to obtain the desired product: crystalline Form 7 of Siponimod fumaric acid (4.63 g).

Example 8

Siponimod (4.5 g) was dissolved in a mixture of 2-methyltetrahydrofuran (21.2 ml) and water (1.4 ml) at 20° C.; the mixture was heated to 30° C. and fumaric acid was added (2.0 g). The mixture was then cooled to 0° C. during 2 h and stirred for additional 2 h; the precipitate was collected by filtration and dried under vacuum at 40° C. to obtain crystalline Form 7 of Siponimod fumaric acid co crystal (3.6 g).

Example 9

To a solution of O-[[4-cyclohexyl-3-(trifluoromethyl)phenyl]methyl]-hydroxylamine (compound A, 264 mg) in of ethyl acetate (3 ml), oxalic acid dihydrate (87 mg) was added, the mixture was stirred overnight at 20° C. to obtain a gel, which was then diluted with ethyl acetate (to about 7 ml). The precipitation was collected by filtration and dried on the filter to obtain form I of the hemioxalate salt of compound A; as shown in FIG. 3.

Example 10

A solution of 0-[[4-cyclohexyl-3-(trifluoromethyl)phenyl]methyl]-hydroxylamine hydrochloride (HCl salt of compound A, 5 g) in methyl-t-butyl ether (25 ml) was stirred with a mixture of saturated aqueous solution of NaHCO$_3$(15 ml) and water (15 ml) for 30 min at 20° C.; the separated organic phase was further washed with water (30 ml), then completely evaporated under vacuum. The residue was dissolved in methyl-t-butyl ether (15 ml) and a hot solution (50-55° C.) of oxalic acid dihydrate in methyl-t-butyl ether (720 mg in 10 ml) was added; Methyl-t-butyl ether (15 ml) was then added to the suspension, which was stirred at 50° C. for 1 h, and then cooled to 0° C. The precipitate was recovered by filtration, washed with methyl-t-butyl ether (10 ml), and dried to obtain form II of the hemioxalate salt of compound A (3.8 g); as shown in FIG. 4.

Example 11

A solution of O-[[4-cyclohexyl-3-(trifluoromethyl)phenyl]methyl]-hydroxylamine hydrochloride (5 g) in dichloromethane (25 ml) was stirred in a mixture of saturated aqueous solution of NaHCO$_3$ (15 ml) and water (15 ml) for 30 min at 20° C.; the separated organic phase was further washed with of water (30 ml) and then completely evaporated under vacuum. The residue was dissolved in dichloromethane (25 ml), oxalic acid dihydrate (720 mg) was added; the mixture was stirred at reflux for 1 h and then cooled to 0° C. The precipitate was collected by filtration and dried on the filter to give form III of the hemioxalate salt of compound A (3.7 g); as shown in FIG. 5.

Example 12

To a solution of compound A (264 mg) in toluene (3 ml), oxalic acid dehydrate (44 mg) was added and the mixture was stirred overnight at 20° C. The precipitate was collected by filtration and dried on the filter to form IV of the hemioxalate salt of compound A as shown in FIG. 6.

Example 13

Form II of the hemioxalate salt of compound A (1 g, prepared according to example 10) was suspended in methanol (1 ml) and stirred for 1 h at 20° C.; the solid was recovered by filtration and dried on the filter to obtain form V of the hemioxalate salt of compound A; as shown in FIG. 7.

The invention claimed is:
1. Crystalline Siponimod fumaric acid, characterized by data selected from one or more of the following:
   a. a PXRD pattern having peaks at 16.4, 17.8, 18.3, 22.7, and 25.4 deg-2-theta±0.2 deg 2-theta;
   b. a PXRD pattern as depicted in FIG. 2;
   c. a PXRD pattern having peaks at 16.4, 17.8, 18.3, 22.7, and 25.4 deg-2-theta±0.2 deg 2-theta, and also having one, two, three, four or five additional peaks selected from 13.6, 14.2, 16.8, 21.8, and 24.4 deg-2-theta±0.2 deg 2-theta;
   d. a solid state $^{13}$C NMR spectrum with characteristic peaks at 146.1, 136.6, 132.8, 130.8, and 128.9 ppm±0.2 ppm;
   e. a solid state $^{13}$C NMR spectrum having the following chemical shift absolute differences from reference peak at 123.5 ppm±1 ppm: 22.6, 13.1, 9.3, 7.3, and 5.4 ppm±0.1 ppm;
   f. a solid state $^{13}$C NMR spectrum as depicted in FIG. 8; and combinations of any a-f.
2. A process of preparing crystalline Siponimod fumaric acid, comprising
   crystallizing Siponimod fumaric acid from trifluoroethanol and water, wherein the crystalline Siponimod fumaric acid is characterized by data selected from one or more of the following:
   a. a PXRD pattern having peaks at 16.4, 17.8, 18.3, 22.7, and 25.4 deg-2-theta±0.2 deg 2-theta;
   b. a PXRD pattern as depicted in FIG. 2;
   c. a PXRD pattern having peaks at 16.4, 17.8, 18.3, 22.7, and 25.4 deg-2-theta±0.2 deg 2-theta, and also having one, two, three, four or five additional peaks selected from 13.6, 14.2, 16.8, 21.8, and 24.4 deg-2-theta±0.2 deg 2-theta;
   d. a solid state $^{13}$C NMR spectrum with characteristic peaks at 146.1, 136.6, 132.8, 130.8, and 128.9 ppm±0.2 ppm;
   e. a solid state $^{13}$C NMR spectrum having the following chemical shift absolute differences from reference peak at 123.5 ppm±1 ppm: 22.6, 13.1, 9.3, 7.3, and 5.4 ppm±0.1 ppm;

f. a solid state $^{13}$C NMR spectrum as depicted in FIG. 8;
and combinations of any a-f.

3. A pharmaceutical composition or formulation comprising crystalline Siponimod fumaric acid according to claim 1.

4. A pharmaceutical composition or formulation according to claim 3 comprising at least one pharmaceutically acceptable excipient.

5. A process for preparing a pharmaceutical composition or formulation according to claim 3 comprising, combining crystalline Siponimod fumaric acid and at least one pharmaceutically acceptable excipient.

6. A method of treating multiple sclerosis, comprising administering an effective amount of crystalline Siponimod fumaric acid according to claim 1, optionally in the form of a pharmaceutical composition or formulation to a subject suffering from multiple sclerosis, or otherwise in need of the treatment.

7. The pharmaceutical composition or formulation according to claim 3, comprising at least one pharmaceutically acceptable excipient, and wherein the pharmaceutical composition is for oral administration.

8. The crystalline Siponimod fumaric acid according to claim 1, characterized by a PXRD pattern having peaks at 16.4, 17.8, 18.3, 22.7, and 25.4 deg-2-theta±0.2 deg 2-theta; and a molar ratio of siponimod to fumaric acid is 1:1.

9. The crystalline Siponimod fumaric acid according to claim 1, characterized by a PXRD pattern as depicted in FIG. 2; and a molar ratio of siponimod to fumaric acid is 1:1.

10. The crystalline Siponimod fumaric acid according to claim 1, characterized by a PXRD pattern having peaks at 16.4, 17.8, 18.3, 22.7, and 25.4 deg-2-theta±0.2 deg 2-theta, and also having one, two, three, four or five additional peaks selected from 13.6, 14.2, 16.8, 21.8, and 24.4 deg-2-theta±0.2 deg 2-theta; and a molar ratio of siponimod to fumaric acid is 1:1.

11. The crystalline Siponimod fumaric acid according to claim 1, characterized by a solid state $^{13}$C NMR spectrum with characteristic peaks at 146.1, 136.6, 132.8, 130.8, and 128.9 ppm±0.2 ppm; and a molar ratio of siponimod to fumaric acid is 1:1.

12. The crystalline Siponimod fumaric acid according to claim 1, characterized by a solid state $^{13}$C NMR spectrum having the following chemical shift absolute differences from reference peak at 123.5 ppm±1 ppm: 22.6, 13.1, 9.3, 7.3, and 5.4 ppm±0.1 ppm; and a molar ratio of siponimod to fumaric acid is 1:1.

13. The crystalline Siponimod fumaric acid according to claim 1, characterized by a solid state $^{13}$C NMR spectrum as depicted in FIG. 8; and a molar ratio of siponimod to fumaric acid is 1:1.

14. The process according to claim 2, comprising:
suspending siponimod hemifumarate Form A in trifluoroethanol,
warming to complete dissolution,
cooling to room temperature, and
adding water to form the crystalline siponimod fumaric acid.

15. The process according to claim 2, wherein the crystalline Siponimod fumaric acid is characterized by a PXRD pattern having peaks at 16.4, 17.8, 18.3, 22.7, and 25.4 deg-2-theta±0.2 deg 2-theta; and a molar ratio of siponimod to fumaric acid is 1:1.

16. The process according to claim 2, wherein the crystalline Siponimod fumaric acid is characterized by a PXRD pattern as depicted in FIG. 2; and a molar ratio of siponimod to fumaric acid is 1:1.

17. The process according to claim 2, wherein the crystalline Siponimod fumaric acid is characterized by a PXRD pattern having peaks at 16.4, 17.8, 18.3, 22.7, and 25.4 deg-2-theta±0.2 deg 2-theta, and also having one, two, three, four or five additional peaks selected from 13.6, 14.2, 16.8, 21.8, and 24.4 deg-2-theta±0.2 deg 2-theta; and a molar ratio of siponimod to fumaric acid is 1:1.

18. The process according to claim 2, wherein the crystalline Siponimod fumaric acid is characterized by a solid state $^{13}$C NMR spectrum with characteristic peaks at 146.1, 136.6, 132.8, 130.8, and 128.9 ppm±0.2 ppm; and a molar ratio of siponimod to fumaric acid is 1:1.

19. The process according to claim 2, wherein the crystalline Siponimod fumaric acid is characterized by a solid state $^{13}$C NMR spectrum having the following chemical shift absolute differences from reference peak at 123.5 ppm±1 ppm: 22.6, 13.1, 9.3, 7.3, and 5.4 ppm±0.1 ppm; and a molar ratio of siponimod to fumaric acid is 1:1.

20. The process according to claim 2, wherein the crystalline Siponimod fumaric acid is characterized by a solid state $^{13}$C NMR spectrum as depicted in FIG. 8; and a molar ratio of siponimod to fumaric acid is 1:1.

* * * * *